United States Patent [19]

Putzig et al.

[11] Patent Number: 4,808,739

[45] Date of Patent: Feb. 28, 1989

[54] CROSS-LINKING TITANIUM & ZIRCONIUM CHELATES & THEIR USE

[75] Inventors: Donald E. Putzig, Newark; Kenneth C. Smeltz, Wilmington, both of Del.

[73] Assignee: E. I. Du Pont de Nemours and Company, Wilmington, Del.

[21] Appl. No.: 31,921

[22] Filed: Mar. 10, 1987

[51] Int. Cl.$^4$ .............................. C07F 3/06; C07F 7/28
[52] U.S. Cl. ........................................ 556/55; 166/308
[58] Field of Search ............................................ 556/55

[56] References Cited

U.S. PATENT DOCUMENTS

| | | | |
|---|---|---|---|
| 2,824,114 | 2/1958 | Bostwick | 260/429.3 |
| 2,824,115 | 2/1958 | Beacham et al. | 260/429.5 |
| 3,457,208 | 7/1969 | Sullivan | 556/55 |
| 3,888,312 | 6/1975 | Tiner | 166/308 |
| 4,077,941 | 3/1978 | Stephen | 556/55 |
| 4,460,751 | 7/1984 | Hanlon et al. | 525/371 |

FOREIGN PATENT DOCUMENTS

| | | | |
|---|---|---|---|
| 589184 | 12/1959 | Canada | 562/567 |
| 2108122 | 5/1983 | United Kingdom . | |

OTHER PUBLICATIONS

Yoshino et al., Bulletin of the Chemical Society of Japan, vol. 46, p. 2899 (1973).

*Primary Examiner*—Michael L. Shippen
*Attorney, Agent, or Firm*—Charles E. Feeny

[57] ABSTRACT

Water-soluble N,N-bis-(2-hydroxyethyl)glycine/metal chelates represented by the formula:

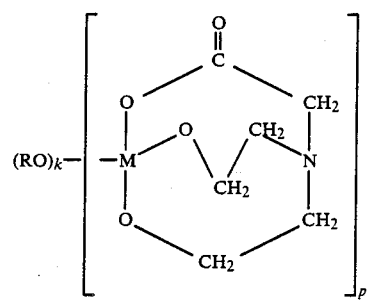

wherein R is H or alkyl (1–12C); M is Ti or Zr; k is a number in the range between 0 and 1, p is a number in the range between 1 and 2, and $k+p=2$ (in particular embodiments: $k=1$ and $p=1$; $k=0$ and $p=2$; and $k=0.5$ and $p=1.5$). The chelates can be used as crosslinking agents in hydraulic fracturing fluids and in gels that are used for selectively plugging permeable zones in subterranean formations or for plugging subterranean leaks.

7 Claims, No Drawings

CROSS-LINKING TITANIUM & ZIRCONIUM CHELATES & THEIR USE

BRIEF SUMMARY OF THE INVENTION

The present invention relates to novel watersoluble titanium and zirconium chelates formed from N,N-bis-(2-hydroxyethyl)-glycine and a titanium or zirconium halide or ester. It relates also to the use of the chelates as cross-linking agents in hydraulic fracturing fluids, and in gels that are used for selectively plugging permeable zones in subterranean formations or for plugging subterranean leaks.

BACKGROUND OF THE INVENTION

Reactions of titanium or zirconium compounds with amino compounds are known. For example, Yoshino et al., in the Bulletin of The Chemical Society of Japan, Vol.46, 2899 (1973), have reported their observations in respect of certain mixtures of titanium and zirconium esters with nitrogen-containing compounds. Boiling a mixture of Zr isopropoxide and glycine dissolved in ethanol for 22 hours gave a white precipitate which was stated to be 2,5-piperazinedione. Substituting DL-alpha-alaline in that mixture, gave a white precipitate which was said to be 3,6-dimethyl-2,5-piperazinedione. When a mixture of glycine and Ti isopropoxide in isopropanol, and mixtures of glycine and Ti n-butoxide in ethanol and isopropanol, were heated to boiling, the glycine did not dissolve completely, but after 20 hours, light brown powders were obtained which were stated to be 2,5-piperazinedione. Moreover, in U.S. Pat. No. 2,824,114, Bostwick disclosed compounds prepared by reacting an alkyl titanium or zirconium ester with a monohydric, dihydric, or trihydric monoamino or diamino alcohol, e.g., di-hydroxyethyl-ethylene diamine, and suggested using his compounds as dispersing agents and as surface active agents for hydrocarbons and waxes. Similarly Beacham et al., in U.S. Pat. No. 2,824,115, disclosed combining organo titanium and organo zirconium compounds with polyhydroxyalkyl alkylene polyamines, and suggested using their compounds as dispersing agents, additives to paint and varnish formulations to improve durability, agents for the treatment of wool and animal fibers, and in various textile and cosmetic applications.

The use of zirconium compounds as cross-linking agents is described by Kucera in U. K. patent application GB No. 2 108 122 A. Kucera disclosed reacting a zirconium alkoxide with a dialkanol amine or trialkanol amine, and suggested using the resulting compounds as cross-linking agents in hydraulic fracturing of subterranean formations. The production of oil and gas can be stimulated by the hydraulic fracturing technique, in which a fluid composition is introduced into an oil or gas well at a flow rate and pressure which create and/or extend a fracture into the oil- or gas-containing formation. The fluid composition usually carries a proppant (e.g., sand, bauxite, etc.) which is forced into the fracture by the fluid composition and prevents closure of the formation after the fluid pressure is released. Tiner et al., in U.S. Pat. No. 3,888,312, provide an example of the use of titanium-containing cross-linking agents in fluid or hydraulic fracturing. They disclosed hydraulic fracturing of subterranean formations using aqueous gels prepared from a solvatable polysaccharide which had been cross-linked with ammonium tetralactotitanate(IV) or bis(triethanolamine)bis(isopropyl)-titanium.

Recovery of oil from subterranean formations frequently involves displacing crude oil with a driving fluid, e.g., gas, water, brine, steam, polymer solution, foam, or micellar solution. Ideally, such techniques (commonly called flooding techniques) would provide a bank of oil of substantial depth being driven to a producing well; in practice, that frequently is not the case. Oil-bearing strata are usually heterogeneous, some parts of them being more permeable to a driving fluid than others. As a consequence, channeling frequently occurs so that the driving fluid flows preferentially through zones depleted of oil (so-called "thief" zones) rather than through those parts of the strata which contain sufficient oil to make oil-recovery operations profitable. High permeability zones can also cause undesirable loss of drilling fluids when a well (e.g., water, oil or waste disposal) is being drilled. Misplaced casing perforations or casing leaks are another cause of channeling of the driving fluid through zones of high permeability in the subterranean formations. In addition, casing leaks sometimes occur in the annular region above the injection or production packer, and need to be dealt with whether the leaks occur in high or low permeability zones.

Hanlon et al., in U.S. Pat. No. 4,460,751, disclose a cross-linking composition and the use of the composition in a method for reducing permeability of subterranean formations to water. They disclose preparing the composition by mixing (1) water, (2) a Zr salt (oxychloride, acetate, tetrachloride, o-sulfate, carbonate), (3) an acid having the formula HO—C(=O)—CH(OH)—R wherein R is H or alkyl (1–3 C) and (4) a amine having the formula $R^1N(R^2)R^3$ wherein $R^1$ is hydroxyalkl (1–3C), $R^2$ is alkyl (1–3 C) or $R^1$, and $R^3$ is H or $R^2$.

The products of the present invention provide advantages over those of the prior art. For example, the titanium- and zirconium-containing compositions of the present invention have extremely slow rates of cross-linking. They can therefore be used at high temperatures and/or at high pH and still effect cross-linking at acceptable rates. Thus, for example, they can be used in a well completion fluid which contains a high level of brine. Consequently, the compositions of the present invention can be used in hotter geologic formations, including those at greater depths in oil and gas wells. In addition, the compositions of the present invention are better suited as cross-linkers than are those of the prior art in cross-linked gels used in hydraulic fracturing fluids and for plugging leaks and selectively plugging permeable zones.

DETAILED DESCRIPTION OF THE INVENTION

The water-soluble N,N-bis(2-hydroxyethyl)glycine/metal chelate of the present invention can be represented by the formula:

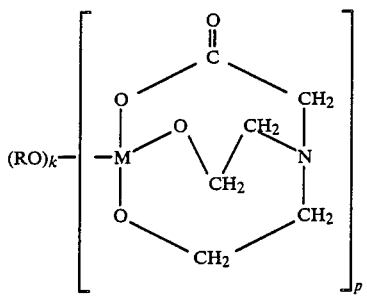

wherein R is H or alkyl (1-12C); M is Ti or Zr; k is a number in the range between 0 and 1, p is a number in the range between 1 and 2, and k+p=2 (in particular embodiments: k=1 and p=1; k=0 and p=2; and k=0.5 and p=1.5).

The water-soluble N,N-bis(2-hydroxyethylglycine/- metal chelates can be prepared by reacting a titanium or zirconium halide or alkoxide with between one and two molar equivalents of N,N-bis-(2-hydroxyethyl)-glycine. Various titanium and zirconium halides and esters can be used for the purposes of the present invention, e.g., Ti(OR)$_4$ or Zr(OR)$_4$ wherein R is alkyl containing 1-12 carbons, TiCl$_4$, ZrCl$_4$, TiOCl$_2$ or ZrOCl$_2$, with ZrOCl$_2$ being preferred. ZrOCl$_2$ may be used as such or it can be formed in situ by reacting ZrCl$_4$ with H$_2$O. N,N-bis(2-hydroxyethyl)-glycine may be present as an amine salt when a Ti or Zr ester is used. The reaction of the titanium and zirconium halides and esters with the glycine derivative can be carried out at a variety of temperatures, e.g., between 15 and 100 degrees C., preferably between 20 and 60 degrees C.

In the hydraulic fracturing process of this invention, one or more fractures is created or extended in an oil- or gas-containing subterranean formation by introducing a cross-linked gel formed from a solvatable polysaccharide into the formation at a flow rate and pressure sufficient to create or extend such a fracture. Another embodiment of the present invention relates to a process for selectively plugging permeable zones in subterranean formations or for plugging subterranean leaks which comprises injecting into the permeable zone or the site of the subterranean leak a cross-linked gel formed from a solvatable polysaccharide. The cross-linking agent for each process is one of the zirconate/N,N-bis-(2-hydroxyethyl)-glycine chelates of this invention.

The solvatable polysaccharides include guar gum and locust bean gum, as well as other galactomannan and glucomannan gums, such as those derived from sennas, Brazilwood, Tera, Honey locust, Karaya gum and the like. Derivatives of gums are useful also, e.g., hydroxyethylguar, hydroxypropylguar, carboxyethylhydroxyethylguar, carboxymethylhydroxypropylguar, and the like, as well as cellulose derivatives containing carboxyl groups, such as carboxmethylcellulose, carboxymethylhydroxyethylcellulose, and the like. Hydroxypropylguar and carboxymethylhydroxypropylguar are preferred polysaccharides for use in the present invention. Hydroxypropylguar is the most preferred gum based upon its commercial availability and desirable properties. On the other hand, carboxymethylhydroxypropylguar is sometimes used in place of hydroxypropylguar in fracturing fluids when the permeability of the formation is such that one wishes to keep the residual solids at a low level, so as to prevent formation damage. The solvatable polysaccharides can be used individually or in combination; usually, however, a single material is used. The solvatable polysaccharides are normally blended with a solvent such as water or an aqueous medium (e.g., aqueous methanol, ethanol, 1 to 3% HCl or potassium chloride) to form an uncrosslinked gel as a first step.

The amounts of solvatable polysaccharide and the cross-linker therefor vary. One uses small but effective amounts which for both will vary with the circumstances, e.g., the type of geologic formation, the depth at which the process (e.g., fluid fracturing, permeable zone plugging or leak plugging) is to be performed, temperature, pH, etc. In all cases, one uses as small an amount of each in water as will provide the viscosity level necessary to effect the desired result, i.e., fracturing of the subterranean formation, or plugging leaks or permeable zones to the extent necessary to promote adequate recovery of oil or gas from it. For example, satisfactory gels can generally be made for fluid fracturing by using the solvatable polysaccharide in amounts up to about 1.2 weight percent and up to about 0.30 weight percent of the cross-linker, both percentages being based on the weight of the aqueous liquid. Preferably, from about 0.4 to about 0.75 weight percent of the solvatable polysaccharide is used and from about 0.05 to about 0.10 weight percent of the cross-linker. For plugging leaks or permeable geologic zones, one generally uses about 0.40 to 1.2 weight percent of a solvatable polysaccharide, preferably 0.40 to 0.75 weight percent, and 0.04 to 0.30 weight percent of the zirconium chelate, preferably 0.05 to 0.10 weight percent.

The following Examples are given in further illustration of the invention but not by way of limitation. Preparation of the compositions in the Examples were carried out in a closed vessel containing an agitator, thermometer, condenser, nitrogen inlet and dropping funnel. Unless specified otherwise, percentages are given by weight.

EXAMPLE 1 (Best Mode)

N,N-bis-(2-hydroxyethyl)-glycine (53.6 mols; 8748.6 g) was added with stirring to aqueous zirconium oxydichloride (53.6 mols; 32,986.8 g of an aqueous solution having a Zr content of 14.8 wt. %) over a period of about 2 hours and 15 minutes, causing the temperature to drop from 23 to 18 degrees C. and giving a clear yellow liquid. The mixture was stirred for about 1 hour more, during which time the pot temperature rose to 20 degrees C. The clear yellow liquid had a pH of about 0.5. Aqueous sodium hydroxide (14128 g of a 30 wt % solution) was added over a period of 4 hours and 10 minutes to a pH of 7.3 and a pot temperature of 42 degrees C. The reaction mixture was heated to 60 degrees C. and held at that temperature for about 2 hours and 20 minutes. Yield =55,367 g of a hazy liquid product containing about 8.83 wt. % Zr and having a density of 1.282 g/ml.

The cross-linking properties of the chelate are given below as a function of the viscosity of hydroxypropylguar cross-linked with the zirconate/bis(2-hydroxyethyl)-glycine chelate of EXAMPLE 1. For a pH 9.9 gel, one blends for 30 minutes in a Waring Blender at a pH of 3.1: a fumaric acid buffer, 4.5 g of hydroxypropylguar and 0.9 g of sodium thiosulfate in 750 ml of 2% by weight KCl. To that gel in a 1500 ml beaker one adds 0.75 ml of cross-linker solution containing 0.00064 mol of zirconium, and mixes vigorously for about 15 seconds to about 3 minutes. A 25 ml sample of that crosslinker containing gel is placed in the cup of the FANN 50 Viscometer with an R-1, B-3 configuration at 250 degrees F. (121 decrees C.) and 100 rpm (88 sec$^{-1}$) shear.

When tested using the foregoing procedure, the chelate of Example 1 gave a crosslinking rate of 11.5 minutes and the viscosities set forth in Table 1.

TABLE 1

| Time (min) | Viscosity (cps) |
|---|---|
| 0 | 132 |
| 5 | 90 |
| 10 | 435 |
| 20 | 402 |
| 30 | 390 |
| 40 | 378 |
| 60 | 369 |
| 90 | 359 |

EXAMPLE 2

N,N-bis-(2-hydroxyethyl)-glycine (1.28 mols; 208.3 g) was added with stirring to aqueous zirconium oxydichloride (1.28 mols; 785.4 g of a 29 wt. % solution) over a period of about 30 minutes, causing the temperature to drop from 23 to 16 degrees C. The mixture was stirred at about 23 degrees for 30 minutes more, during which time the temperature of the mixture rose to 23 degrees C. The resulting clear yellow liquid had a pH of about 0.5. Aqueous sodium hydroxide (387 g of a 30 wt % solution) was added over a period of 30 minutes to a pH of 7.4, while maintaining the pot temperature at about 20 degrees C. by use of an ice bath. The reaction mixture was heated to 60 degrees C. and held at that temperature for about 2 hours. Yield =1365.6 g of a water clear product containing about 8.85 wt. % Zr and having a density of 1.281 g/ml.

EXAMPLE 3

The procedure of EXAMPLE 2 was repeated at a N,N-bis-(2-hydroxyethyl)-glycine/zirconium oxydichloride molar ratio of 2/1, resulting in a liquid product having a Zr content of 7.31 wt. % and a density of 1.282 g/ml.

EXAMPLE 4

Methanol (250 ml) was added with stirring to N,N-bis(2-hydroxyethyl)-glycine (0.254 mol; 40.8 g) to give a chalky-white suspension. Over a period of one hour, zirconium tetra-n-propoxide (0.125 mol; 56.5 g of a solution in n-propanol containing 21.5 wt. % Zr) was added with stirring at 50 degrees C . Stirring was continued for two additional hours at 50 degrees. Heating and stirring were discontinued and the reaction mixture was allowed to stand overnight, giving a yellow liquid product, the upper two/thirds of which was clear, and the lower one/third of which contained white solids. The reaction mixture was heated to reflux and additional methanol (150 ml) was added. After two more hours at reflux, a clear yellow liquid product (360.7 g), containing 3.2 wt. % Zr and having a density of 0.866 g/ml, was obtained.

EXAMPLE 5

The procedure of EXAMPLE 4 was repeated at a N,N-bis-(2-hydroxyethyl)-glycine/zirconium n-propoxide mol ratio of 1/1 to give a slightly hazy yellow liquid product containing 5.4 wt. % Zr and having a density of 0.88 g/ml.

EXAMPLE 6

N,N-bis-(2-hydroxyethyl)-glycine (0.15 mol; 24.2 g) was added with stirring at about 20 degrees C. to a mixture of triethyl amine (0.2 mol; 21.2 g) and methanol (40 ml). After heating to reflux (about 60 degrees C.) and adding 16 ml of water, the resulting amine salt of the glycine derivative went into solution. The solution was cooled to 40 degrees C., and tetrakis-(isopropoxy)-Ti (0.1 mol; 28.4 g) was added dropwise with stirring. After stirring an additional hour at 40 degrees C., the clear liquid product (107.9 g) was bottled. Upon standing overnight, some solids separated from the liquid product. Addition of 4.2 g of water gave a clear solution (112.1 g) containing 4.3 wt% Ti and having a density of 1.017 g/ml.

EXAMPLE 7

The procedure of EXAMPLE 6 was repeated at a N,N-bis-(2-hydroxyethyl)-glycine/tetrakis-(isopropoxy)Ti molar ratio of 2/1, giving a clear solution having a Ti content of 3.1 wt. % and a density of 0.99 g/ml.

What is claimed is:

1. A water-soluble N,N-bis-(2-hydroxyethyl)-glycine/metal chelate represented by the formula:

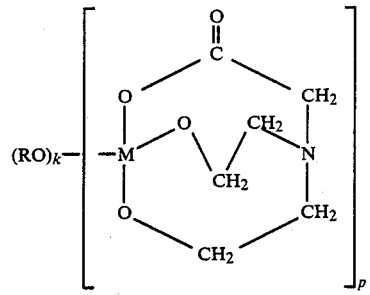

wherein R is H or alkyl (1–12 C.); M is Ti or Zr; k is a number in the range between 0 and 1, p is a number in the range between 1 and 2, and k+p=2.

2. The chelate of claim 1 wherein M is Zr.
3. The chelate of claim 2 wherein each of k and p is 1.
4. The chelate of claim 1 wherein M is Ti.
5. The chelate of claim 2 wherein k is 0 and p is 2.
6. The chelate of claim 4 wherein k is 0 and p is 2.
7. The chelate of claim 4 wherein k is 0.5 and p is 1.5.

* * * * *